US00PP32549P2

(12) United States Plant Patent
Dirr et al.

(10) Patent No.: US PP32,549 P2
(45) Date of Patent: Dec. 1, 2020

(54) ***HYDRANGEA* PLANT NAMED 'BAILPANONE'**

(50) Latin Name: *Hydrangea paniculata*
Varietal Denomination: Bailpanone

(71) Applicant: Bailey Nurseries, Inc, St. Paul, MN (US)

(72) Inventors: Michael A. Dirr, Bogart, GA (US); Jeff Beasley, Lavonia, GA (US); Mark Griffith, Watkinsville, GA (US); Rhonda Helvick, Madison, GA (US); Oren McBee, Bishop, GA (US); David Jonathan Roberts, Athens, GA (US); Justin Schulze, Athens, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 16/873,063

(22) Filed: Jan. 25, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea paniculata* plant named 'Bailpanone' that is characterized by its compact plant size reaching 0.9 to 1.2 m in height and spread, its late blooming habit, its panicles that are creamy white in color and change to light pink in color as they age in northern climates, and its dense panicles with few fertile flowers.

2 Drawing Sheets

Botanical classification: *Hydrangea paniculata.*
Varietal denomination: 'Bailpanone'.

BACKGROUND OF THE INVENTION

The present invention relates to a new and distinct cultivar of *Hydrangea paniculata* and will be referred to hereafter by its cultivar name, 'Bailpanone'. 'Bailpanone' represents a new *Hydrangea*, a perennial shrub grown for landscape use and as a potted plant.

'Bailpanone' derived from an ongoing controlled breeding program directed by the Inventors in Watkinsville, Ga. An objective of the breeding program included developing a new cultivar of *Hydrangea* with a compact plant habit, a heavy blooming habit, and high heat tolerance in southern climates.

'Bailpanone' originated as a seedling that arose from seed derived from open pollination of *Hydrangea* 'PIIHP-I' (U.S. Plant Pat. No. 23,387) in summer of 2012. The male parent is therefore unknown. 'Bailpanone' was selected as a single unique plant from amongst the resulting seedlings in summer of 2013.

Asexual propagation of the new cultivar was first accomplished by softwood stem cuttings by one of the Inventors in summer of 2014 in Watkinsville, Ga. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailpanone' as a unique cultivar of *Hydrangea paniculata.*

1. 'Bailpanone' exhibits a compact plant habit, reaching 0.9 to 1.2 m in height and spread.
2. 'Bailpanone' exhibits a late blooming habit.
3. 'Bailpanone' exhibits panicles that are creamy white in color and change to light pink in color as they age in northern climates.
4. 'Bailpanone' exhibits dense panicles with few fertile flowers.

The female parent of 'Bailpanone' differs from 'Bailpanone' in having an earlier blooming period and flower panicles that are wider at the base. 'Bailpanone' can be most closely compared to the *Hydrangea paniculate* cultivars 'ILVOBO' (U.S. Plant Pat. No. 22,782) and 'Rensun' (U.S. Plant Pat. No. 25,438). Both are similar to 'Bailpanone' in having a compact plant habit and sterile flower sepals that are white when opening. 'ILVOBO' differs from 'Bailpanone' in blooming 3 to 4 weeks earlier and in having flower panicles that are more open with less sterile flowers, and sterile flower sepals that change to light pink and green when mature. 'Rensun' differs from 'Bailpanone' in having a larger plant size, earlier blooming period, and sterile flower sepals that age to dark reddish pink in color.

BRIEF DESCRIPTION OF THE DRAWINGS

The accompanying colored photographs illustrate the overall appearance and distinct characteristics of the new *Hydrangea*. The photographs were taken of a four-year-old plant of 'Bailpanone' as grown in a trial garden in Newport, Minn.

The photograph in FIG. 1 provides a side view of the plant habit of 'Bailpanone' in bloom.

Figure 1:
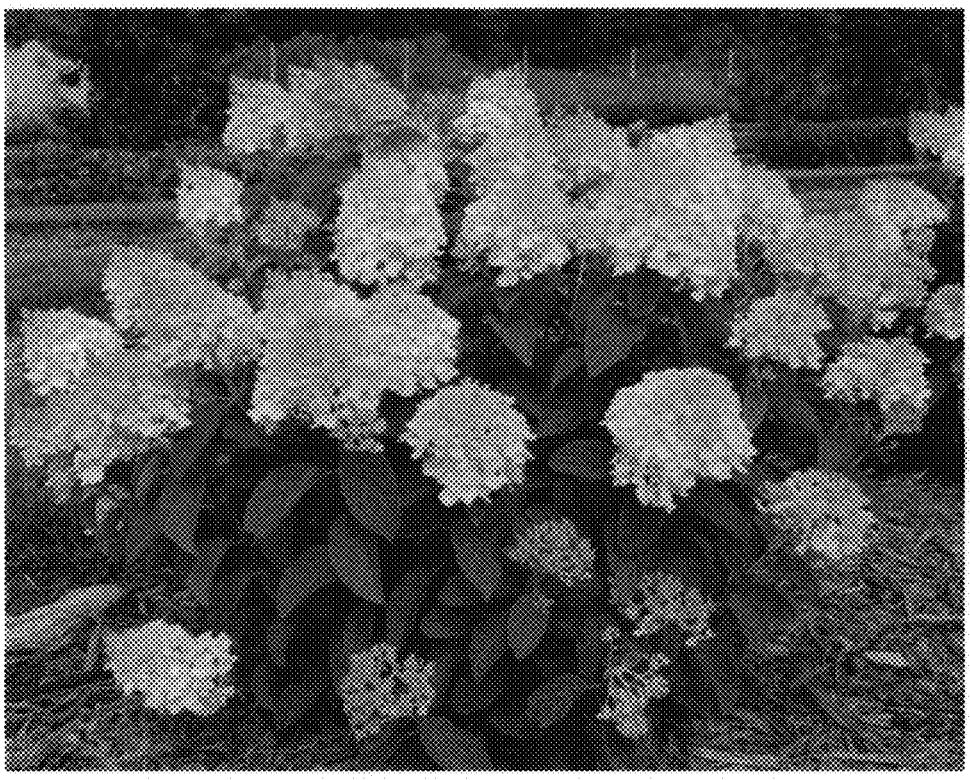
Figure 2:
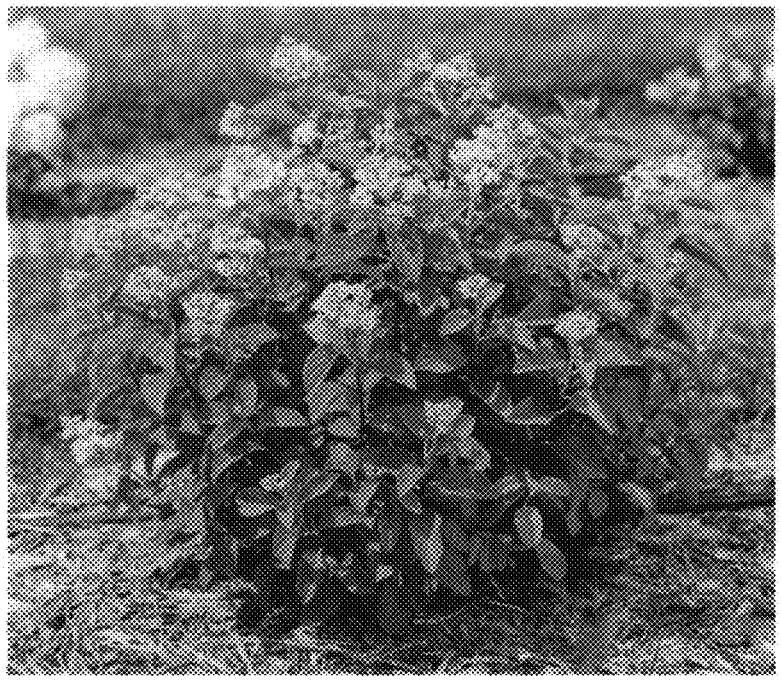

The photograph in FIG. 2 provides a side view of 'Bailpanone' when blooms are opening.

Figure 3:
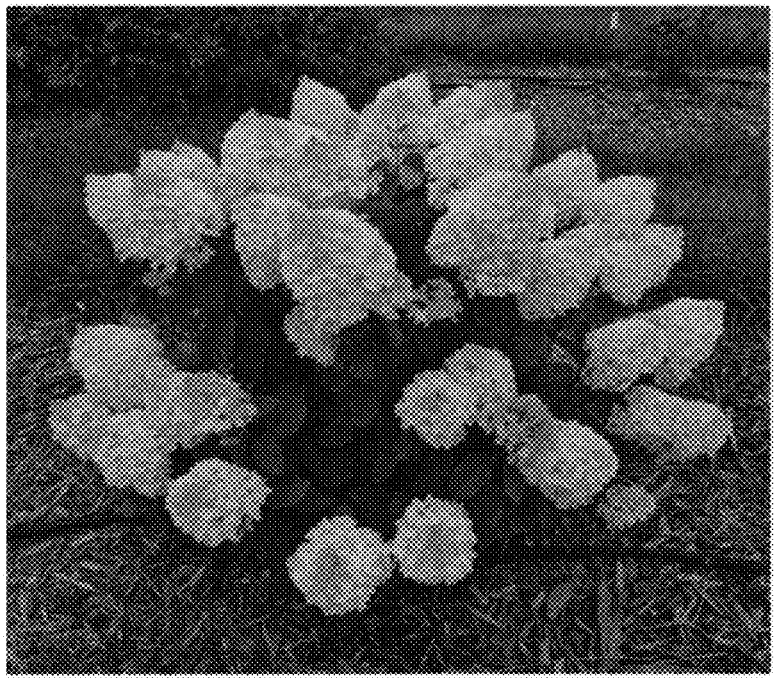

The photograph in FIG. 3 provides a side view of 'Bailpanone' when blooms are fully mature.

Figure 4:
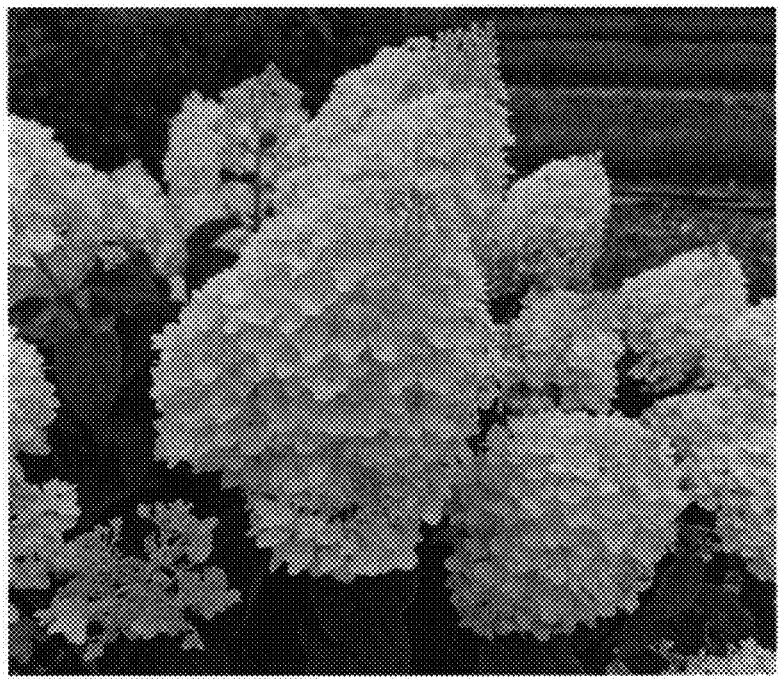

The photograph in FIG. 4 provides a side view of 'Bailpanone' when blooms are aging.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of two-year-old plants of 'Bailpanone' as grown in a greenhouse and outdoors in 2-gallon containers in Newport, Minn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—6 weeks beginning in early August in Minnesota.

*Plant type.*—Deciduous shrub, panicle type *Hydrangea.*

*Plant habit.*—Compact.

*Height and spread.*—Reaches 0.9 to 1.2 m in height and spread as a 4-year-old plant in the landscape.

*Cold hardiness.*—At least to U.S.D.A. Zone 3.

*Diseases and pests.*—No susceptibility and resistance to diseases or pests has been observed.

*Root description.*—Fine, fibrous and dense, NN155A and 164A in color.

*Propagation.*—Softwood stem cuttings.

*Root development.*—An average of 5 weeks for root initiation with a young rooted plant produced in an average of 15 weeks.

*Growth rate and vigor.*—Slow to moderate.

Stem description:

*Stem shape.*—Rounded.

*Stem strength.*—Strong.

*Stem color.*—Young; 145A, mature; a blend of N199A and 200A with internodes tinged with 178A, bark; 199A and 138A.

*Stem size.*—Main stem at base an average of 2 cm in length and 1.5 cm in diameter, lateral branches an average of 24 cm in length (excluding inflorescence) and 5 mm in diameter.

*Stem surface.*—Young stems are matte and densely covered with stiff hairs; average of 0.5 mm in length that match surface color, mature stems are matte and moderately covered with lenticel; an average of 2 mm in length and 1 mm in diameter, 155A in color.

*Stem aspect.*—Slightly outward.

*Internode length.*—An average of 3 cm.

*Branching.*—Freely branching with an average of 10 lateral branches.

Foliage description:

*Leaf shape.*—Ovate to broadly ovate.

*Leaf arrangement.*—Opposite.

*Leaf division.*—Simple.

*Leaf base.*—Retuse to truncate.

*Leaf apex.*—Apiculate to acute.

*Leaf margins.*—Coarsely dentate to serrate.

*Leaf venation.*—Pinnate, color; color upper surface N144A, lower surface matches leaf color.

*Leaf size.*—An average of 9 cm in length and 6 cm in width.

*Leaf attachment.*—Petiolate.

*Leaf number.*—An average of 18 per lateral stem.

*Leaf surface.*—Both surfaces; matte and slightly rugose, upper surface very sparsely covered with short stiff hairs; average of 0.4 mm in length and NN155D in color.

*Leaf color.*—Young upper surface; 144A, mature upper surface; NN137B young and mature lower surface; 191A.

*Petioles.*—An average of 1.5 cm in length and 2 mm in diameter, upper surface color 145A and flushed with 183C, lower surface color 144A and 145C, both surfaces are slightly glossy with upper surface densely covered with very short stiff hairs that match surface color and are 0.2 mm in length, lower surface is covered with a combination of very minute hairs and lenticels, average of 0.2 mm in length that match surface color.

Inflorescence description:

*Inflorescence type.*—Terminal conical panicle, comprised of sterile flowers above fertile flowers.

*Lastingness of inflorescence.*—Sterile flowers; persistent for an average of 6 weeks, fertile flowers; self-cleaning, an average of 5 days.

*Inflorescence number.*—One per lateral stem.

*Inflorescence size.*—An average of 22 cm in height and 15.5 cm in diameter.

*Flower number.*—An average of 210 sterile flowers and 70 fertile flowers per panicle.

*Flower fragrance.*—None.

*Flower aspect.*—Sterile flowers; held upright to outward from peduncle, densely packed, fertile flowers; held upright from peduncle.

*Flower size.*—Sterile flowers; up to 4.5 cm in diameter (average of 3.2 cm in diameter) and 1.3 cm in depth, fertile flowers; an average of 5 mm in diameter and depth.

*Flower type.*—Sterile flowers rotate, fertile flowers campanulate.

*Flower buds.*—Sterile flowers; an average of 4.5 mm in length and 6 mm in diameter, globose in shape, 155C in color, fertile flowers; an average of 3 mm in length and 3.5 mm in diameter, broad obovate in shape, 150D in color.

*Peduncles.*—Primary peduncles; strong, flattened oval in shape, an average of 3 cm in length and 2 mm in width. secondary peduncles 21.5 cm in length and 2.5 mm in width, 144B to 144D in color, surface densely pubescent surface covered with thin pubescence an average of 0.2 mm in length and too small to measure color.

*Pedicels.*—Sterile flowers; moderate strength, an average of 1.5 cm in length and 1.5 mm in width, 157A in color, surface is pubescent, held at variable angles to peduncle, an average of 2 petiole leaves; narrowly elliptic in shape, about 4 mm in length and 2.5 mm in width, finely pubescent on both surfaces, cuneate base, acute apex, 157A in color, fertile flowers; minute; an average of 0.2 mm in length and width, strong, 157A in color, pubescent surface.

*Fertile flowers*.—Campanula in shape, only pistils, ovary and sepals persistent, petals; drop quickly as the flower matures, 5, ovate in shape, NN155B in color on both surfaces, glabrous on both surfaces, acute apex, truncate base, average of 2 mm in length and 1.5 mm in width, sepals; 5 fused in campanulate calyx, average of 2.1 mm in length and 2.5 mm in width, free triangular-shaped tips about 0.4 mm in width and length, 144D in color and glabrous on both surfaces.

*Sterile flowers*.—Sepals; 4 (rarely 5), un-fused, rotate with margins overlapping, broadly oval in shape, held slightly upright and slightly concave, rounded apex and occasionally with small notch, rounded base, entire margins, up to 1.8 cm in length and 1.5 cm in width, both surfaces; glabrous and matte, color when opening and fully open upper and lower surface NN155A and changing to 144D in late summer, color in fall A blend of 144D and 146D on upper and lower surface with lower surface partially suffused with 183C, petals; folded inward into petal spot, 1.5 mm in diameter, 1 mm in depth, NN155B in color with a glabrous surface on both surfaces, drop as flowers mature.

Reproductive organs:

*Presence*.—On fertile flowers (very rare and malformed if present on sterile flowers).

*Gynoecium*.—3 pistils, an average of 1 mm in length, stigma; club-shaped and 155A in color, style; 0.75 mm in length, 145D in color, ovary is 144C in color.

*Androecium*.—An average of 8 stamens, filaments; an average of 3 mm in length and NN155C in color, anthers; broad oblong in shape, an average of 0.7 mm in length and 145D in color, pollen; moderate in quantity and 158D in color.

*Fruit and seed*.—None observed to date.

It is claimed:

1. A new and distinct cultivar of *Hydrangea* plant named 'Bailpanone' substantially as herein illustrated and described.

* * * * *